US005849863A

United States Patent [19]
Stewart et al.

[11] Patent Number: 5,849,863
[45] Date of Patent: Dec. 15, 1998

[54] CYTOLYTIC BRADYKININ ANTAGONISTS

[75] Inventors: John M. Stewart; Daniel C. Chan, both of Denver; Eric T. Whalley, Golden; Lajos Gera, Denver, all of Colo.

[73] Assignees: University of Colorado, Boulder; Cortech, Inc., Denver, both of Colo.

[21] Appl. No.: 526,065

[22] Filed: Sep. 8, 1995

[51] Int. Cl.$^6$ .................................................. C07K 99/18
[52] U.S. Cl. .......................................................... 530/314
[58] Field of Search ..................... 530/314, DIG. 600, 530/DIG. 601, DIG. 602

[56] References Cited

U.S. PATENT DOCUMENTS

| | | | |
|---|---|---|---|
| 4,693,993 | 9/1987 | Stewart et al. | 514/14 |
| 5,648,336 | 7/1997 | Stewart et al. | 514/15 |
| 5,700,779 | 12/1997 | Goodfellow et al. | 514/14 |

FOREIGN PATENT DOCUMENTS

| | | | |
|---|---|---|---|
| WO 89/01781 | 3/1989 | WIPO | A61K 37/42 |
| 0 370 453 A2 | 5/1990 | WIPO | C07K 7/18 |

OTHER PUBLICATIONS

Bunn, P. A., "Neuropeptide Signal Transduction in Lung Cancer: Clinical Implications of Bradykinin Sensitivity and Overall Heterogeneity," *Cancer Res.*, 52, 24–31 (1992).

Bunn, P. A., et al., "Effects of Neuropeptide Analogues on Calcium Flux and Proliferation in Lung Cancer Cell Lines," *Cancer Res.*, 54, 3602–3610 (1994).

Bunn, P. A., et al., "Neuropeptide Stimulation of Calcium Flux in Human Lung Cancer Cells: Delineation of Alternative Pathways," *Proc. Natl. Acad. Sci. USA*, 87, 2162–2166 (1990).

Cheronis, J. C., et al., "A New Class of Bradykinin Antagonists: Synthesis and In Vitro Activity of Bissuccinimidoalkane Peptide Dimers," *J. Med. Chem.*, 35, 1563–1572 (1992).

Stewart, J. M., et al., "Bradykinin Chemistry: Agonists and Antagonists," In:*Adv. Exp. Med. Biol.*, vol. 156, Fritz, H., (ed.), Plenum Press, New York, pp.585–589 (1983).

Vavrek, R. J., et al., "Succinyl Bis–Bradylinins: Potent Agonists with Exceptional Resistance to Enzymatic Degradation," In: *Peptides—Structure and Function*, Hruby, V. J., et al., (eds.), Pierce Chemical Company, Rockford, IL, pp.381–384 (1983).

Hawleys Condensed Chemical Dictionary, p. 1098 12th Edition (1993) "*Suberic Acid*".

*Primary Examiner*—Cecilia J. Tsang
*Assistant Examiner*—Patrick R. Delaney
*Attorney, Agent, or Firm*—Cushman Darby & Cushman IP Group of Pillsbury Madison & Sutro LLP

[57] ABSTRACT

The present invention provides bradykinin antagonists effective to inhibit cancer cell growth. Also provided are methods of inhibiting lung cancer cell growth by administering a therapeutically effective amount of a dimerized bradykinin antagonist.

20 Claims, 2 Drawing Sheets

CYTOLYTIC BRADYKININ ANTAGONISTS

BACKGROUND OF THE INVENTION

Bradykinin (BK) is a potent inflammatory peptide whose generation in tissues and body fluids elicits many physiological responses including vasodilation, smooth muscle spasm, edema, as well as pain and hyperalgesia (Burch et al., "Molecular Biology and Pharmacology of Bradykinin Receptors", Landes Comp. (1993); Burch, edited: "Bradykinin Antagonists", Dekker (1991)). There is increasing evidence that BK and related kinins contribute to the inflammatory response in acute and chronic diseases including allergic reactions, arthritis, asthma, sepsis, viral rhinitis, and inflammatory bowel disease. Recently BK was implied to be involved as an autocrine in the pathogenesis of human lung cancer (Bunn et al., *Proc Natl. Acad.Sci. USA* 87:2162–2166 (1990); Bunn et al., *Cancer Research* 52:24–31 (1992)). BK has been shown to be the most potent peptide stimulant of intracellular $Ca^{++}$ release in the highest fraction of human lung cancer cell lines (Bunn et al., *Cancer Research* 52:24–31 (1992)). The design and synthesis of specific, potent and stable bradykinin antagonists (BKA) has long been considered a desirable goal in medicinal chemistry. In the past few years, efforts have been directed towards the development of potent BK antagonists as a means for the chemoprevention and therapeutic treatment of human lung cancers.

Lung cancer is the second most common and the most lethal cancer in the United States. A large fraction of lung cancers (all small cell lung cancers (SCLC), some adenocarcinomas and a few squamous carcinomas) have a neuroendocrine phenotype (Becker et al., "The Endocrine Lung in Health & Disease", Saunders (1984)). These cancers and their premalignant precursors utilize a neuropeptide autocrine/paracrine growth factor pathway, i.e., they produce a variety of neuropeptides, express cell surface receptors for these peptides, and show autocrine stimulation by these peptides. Over the years, a number of specific and potent neuropeptide antagonists (including bradykinin, bombesin, cholecystokinin and many others) and anti-peptide antibodies were developed and used in an attempt to inhibit the growth of the lung cancer cells which expressed receptors for these specific neuropeptides (Bunn et al., *Cancer Research* 54:3602–3610 (1994)). However, this approach failed to inhibit a majority of lung cancer cells because of the heterogeneity of neuropeptide receptor expression among the lung cancer cells.

It has been shown that broad spectrum substance P derivatives inhibited the growth of several lung cancer cell lines. However, very high concentrations (>40 µM) of these compounds were required, presumably because this interference occurs at the downstream level of the signal pathway (Bunn et al., *Cancer Research* 54:3602–3610 (1994)). It is thus desirable to provide neuropeptide antagonists with improved potency and specificity.

SUMMARY OF THE INVENTION

The present invention provides bradykinin (BK) antagonist dimers capable of inhibiting cancer cell growth. These dimers are generally described by the formula:

$$BKA_1—X—BKA_2, \quad (I)$$

wherein $BKA_1$, and $BKA_2$ are bradykinin antagonists and X is a linker group. $BKA_2$ is optionally absent (Formula II) thus providing an effective bradykinin antagonist comprising a BKA monomer and a linker.

Further provided, and also effective in inhibiting cancer cell growth, are compounds comprising a bradykinin antagonist and a neurokinin receptor antagonist according to the formula:

$$BKA—X—Y; \quad (III)$$

wherein BKA is a bradykinin antagonist peptide;

X is a linker; and

Y is neurokinin receptor antagonist.

In addition, the present invention provides dimerized neurokinin receptor antagonists:

$$Y_1—X—Y_2 \quad (IV)$$

wherein $Y_1$ and $Y_2$ are the same or different neurokinin receptor antagonists.

The invention further provides oligomers comprising 3 or more BKA's of the formula $$(BKA)_n—X \quad (V)$$

where n is a whole number greater than 2.

Also provided by the invention are methods of inhibiting lung cancer cell growth by administering to a subject afflicted with lung cancer, a therapeutically effective amount of one or more of the compounds according to Formulas I, II, III, IV or V.

DETAILED DESCRIPTION OF THE INVENTION

The present invention is based on the discovery that certain dimerized bradykinin antagonist peptides are highly effective in inhibiting the growth of cancer cells, particularly lung cancer cells, i.e., small cell lung sarcinoma. These dimers comprise antagonists which are analogs of the bradykinin peptide ($Arg^1$-$Pro^2$-$Pro^3$-$Gly^4$-$Phe^5$-$Ser^6$-$Pro^7 Phe^8$-$Arg^9$). A majority of antagonists known in the art represent modifications whereby DPhe has been substituted with LPro in position 7 of the BK sequence and are selective against the B2 class of BK receptor, which is expressed in most of the human lung cancer cell lines. Many of these analogs, with or without pseudo-peptide bond modifications, were found to be specific and stable but only exhibited moderate potency in calcium flux assays. It has been found by the present inventors that a series of BKA dimers based on the classical B2 receptor antagonists with DPhe substitution (Cheronis et al., *J. Med.Chem.* 35:1563–1572 (1992)) have improved potency and stability.

A third generation of BK antagonists (Burch et al., "Molecular Biology and Pharmacology of Bradykinin Receptors", Landes Comp. (1993)) containing modified amino acids (Tic, Oic, Igl, Nig) in positions 5, 7, and 8 of BK's primary sequence were synthesized and found to be several orders of magnitude more potent B2 receptor antagonists than the classical DPhe7 substituted analogues in various assays in vitro. Unfortunately, even at very high concentrations all of these BK antagonists failed to show any growth inhibitory effects in the human lung cancer cell lines, presumably due to the receptor heterogeneity.

A further class of BK antagonist dimers were synthesized by cross linking the third generation BK antagonists. This modification not only increased the potency and stability of these B2 receptor antagonists, but several of this new class of antagonists were able to inhibit the growth of human lung cancer cells completely even at concentrations of 10 μM or less. Furthermore, preliminary studies have shown that lung cancer cell lines are more sensitive to the cytotoxic effects of these new antagonists than those of normal epithelial and fibroblast cell lines. It has also been found that these new antagonists induce apoptosis in the treated lung cancer cells.

The dimers may be represented by the formula $$BKA_1-X-BKA_2, \qquad (I)$$

wherein $BKA_1$ and $BKA_2$ are bradykinin antagonists and X is a linker. Preferably, $BKA_1$ and $BKA_2$ are independently selected from the following:

Arg-Pro-Pro-Gly-Phe-Ser-Pro-Phe-Arg (SEQ ID NO:1);
DArg-Arg-Pro-Hyp-Gly-Thi-Ser-DTic-Nig-Arg;
DArg-Arg-Pro-Hyp-Gly-Igl-Ser-DIgl-Oic-Arg;
Cys-DArg-Arg-Pro-Hyp-Gly-Igl-Ser-DIgl-Oic-Arg;
ε-Lys-DArg-Arg-Pro-Hyp-Gly-Igl-Ser-DIgl-Oic-Arg;
Gun-Gly-ε-Lys-Arg-Pro-Pro-Gly-Phe-Ser-Pro-Leu (SEQ ID NO:2);
Dhq-DArg-Arg-Pro-Hyp-Gly-ε-Lys-Ser-DCpg-CPg-Arg;
Dhq-ε-Lys-DArg-Arg-Pro-Hyp-Gly-Cpg-Ser-DCpg-CPg-Arg;
DArg-Arg-Pro-Hyp-Gly-Cpg-Ser-DCpg-CPg;
DArg-Cys-Pro-Hyp-Gly-Cpg-Ser-DCpg-Cpg;
DArg-Lys-Pro-Hyp-Gly-Cpg-Ser-DCpg-Cpg;
DArg-Arg-Pro-Hyp-Gly-Cpg-Ser-Tic-Cpg;
DArg-Arg-Pro-Hyp-Gly-Thi-Ser-Tic-Cpg;
DArg-Arg-Pro-Hyp-Gly-Cpg-Ser-DTic-Cpg;
DArg-Arg-Pro-Hyp-Gly-Thi-Ser-DTic-Cpg;
DArg-Arg-Pro-Hyp-Gly-Igl-Ser-DIgl-Oic;
  Arg-Pro-Hyp-Gly-Igl-Ser-DIgl-Leu;
DArg-Arg-Pro-Hyp-Gly-Igl-Ser-DIgl-Leu;
Gun- DArg-Arg-Pro-Hyp-Gly-Igl-Ser-DIgl-Oic;
DArg-Arg-Pro-Hyp-Gly-Thi-Ser-DIgl-Oic;
Gun- DArg-Arg-Pro-Hyp-Gly-Thi-Ser-DIgl-Oic;
DArg-Arg-Pro-Hyp-Gly-Igl-Ser-DTic-Cpg;
Lys-Arg-Pro-Hyp-Gly-Igl-Ser-DTic-Cpg;
Lys-Arg-Pro-Hyp-Gly-Igl-Ser-DIgl-Oic;
Lys- Lys-Arg-Pro-Hyp-Gly-Igl-Ser-DIgl-Oic; and
DArg-Arg-Pro-Hyp-Gly-Thi-Ser-DTic-Oic.

The linker X may be any linking group which does not interfere with the inhibitory activity of the monomer-linker or dimerized product using ester, imido-ester, and thio-ester based linking agents, for example. X may be an N-terminal acylating or cross-linking group including a bissuccinimidoalkane such as bissuccinimidohexane; bissuccinimidoalkene; bissuccinimidoamine; bis(imidyl)alkenyl or -alkyl such as suberimidyl; aminocaproic acid-succinyl; dicarboxylic acid derivatives such as succinyl and suberyl; epsilon-succinimido-N-caproyl; and methoxy-suberimido-based linker. The alkane groups may be substituted with, for example, carbonly and/or amino groups. Polyoxyethylene linkers may also be used.

With regard to linker length, there appears to be a correlation between linker length and cytotoxicity, i.e., the longer the linker, the higher the potency of the compound. Therefore, the linker may comprise alkyl chains 6 carbons in length or greater. Alkyl chains of 8 carbons or more are preferred, with those of 12 to 18 carbons being most preferred. Chain lengths of greater than 18 carbons may also be used. Examples of such preferred linker groups include bissuccinimidohexane, bissuccinimidooctane, bissuccinimidononane and bissuccinimidodecane.

The monomers may be linked at any position of the BKA. For example, linking may be achieved via the N-terminus, either through the terminal arginine or through an added lysine residue. Alternatively, serine, if present, may be substituted with cysteine or lysine for internal linkage via the S or N of the side chain, respectively. It is preferred that there be at least one basic charge at the amino end of the dimerized or monomer-linker compounds. For example, the charge may be on the amino group of an N-terminal lysine residue or on the imide group of the linker.

In a particular embodiment, the bradykinin antagonist dimer is selected from:

B2120 Suc—(Arg—Pro—Pro—Gly—Phe—Ser—Pro—Phe—Arg)$_2$

B2124 Suc—(Eac—Eac—Arg—Pro—Pro—Gly—Phe—Ser—Pro—Phe—Arg)$_2$

B9830 Suim-(DArg—Arg—Pro—Hyp—Gly—Thi—Ser—DTic—Nig—Arg)$_2$

B9832 Sub—(DArg—Arg—Pro—Hyp—Gly—Thi—Ser—DTic—Nig—Arg)$_2$

B9836 BSH-(S—Cys—DArg—Arg—Pro—Hyp—Gly—Igl—Ser—DIgl—Oic—Arg)$_2$

CP-0127 DArg—Arg—Pro—Hyp—Gly—Phe—Cys—DPhe—Leu—Arg—COOH
                                              |
                                             BSH
                                              |
         DArg—Arg—Pro—Hyp—Gly—Phe—Cys—DPhe—Leu—Arg—COOH

B168 Eac—DArg—Arg—Pro—Hyp—Gly—Thi—Ser—DIgl—Oic—Arg.TFA
     |
     Suc—DArg—Arg—Pro—Hyp—Gly—Thi—Ser—DIgl—Oic—Arg.TFA

B196 DArg—Arg—Pro—Hyp—Gly—Igl—Cys—DIgl—Oic—Arg.TFA
                              |
     DArg—Arg—Pro—Hyp—Gly—Igl—Cys—DIgl—Oic—Arg.TFA;

-continued where
BMH=Bismaleimidohexane
EAC-SUC=Aminocaproic acid-succinyl
SUB=Suberyl
SUIM=Suberimidyl
MOSI=Methoxy-suberimido
BSH=Bissuccinimidohexane
ESC=Epsilon-Succinimido-N-Caproyl
TFA=Trifluoroacetic acid
SUC=Succinyl.

In a more preferred embodiment, BKA$_1$ and BKA$_2$ are selected from

DArg—Arg—Pro—Hyp—Gly—Igl—Ser—DIgl—Oic—Arg, and

Lys—DArg—Arg—Pro—Hyp—Gly—Igl—Ser—DIgl—Oic—Arg.

Preferably, BKA$_1$—X—BKA$_2$ is

Lys—DArg—Arg—Pro—Hyp—Gly—Igl—Ser—DIgl—Oic—Arg
|
SUB
|
Lys—DArg—Arg—Pro—Hyp—Gly—Igl—Ser—DIgl—Oic—Arg; or

DArg—Arg—Pro—Hyp—Gly—Igl—Ser—DIgl—Oic—Arg
|
SUIM
|
DArg—Arg—Pro—Hyp—Gly—Igl—Ser—DIgl—Oic—Arg.

The present invention also provides compounds of the formula

BKA—X, (II)

where BKA and X are as previously described.

Preferred compounds according to Formula II include
MOSI-Lys-Lys-Arg-Pro-Hyp-Gly-Igl-Ser-DIgl-Oic;
MOSI-DArg-Arg-Pro-Hyp-Gly-Igl-Ser-DIgl-Oic-Arg; and
MOSI-DArg-Arg-Pro-Hyp-Gly-Thi-Ser-DTic-Oic-Arg.

Further provided are compounds of the formula

BKA—X—Y, (III)

wherein BKA is a bradykinin antagonist peptide;
X is a linker; and
Y is a neurokinin receptor antagonist.

Any neurokinin receptor antagonist known in the art may be used in these heterodimeric embodiments. Such antagonists are described, for example, in Langdon et al., *Cancer Research* 52: 4554–4557 (1992); Orosz et al., *Int. J. Cancer* 60:82–87 (1995); and Woll et al., *Cancer Research* 50:3968–3973 (1990). Some of these monomeric antagonists have demonstrated inhibitory activity against small cell lung cancer.

By way of example, Y may be selected from
Asp-Tyr-DTrp-Val-DTrp-DTrp-Arg-CONH$_2$;
Cys-Tyr-DTrp-Val-DTrp-DTrp-Arg-CONH$_2$;
DArg-DArg-Lys-Pro-Lys-Asn-DPhe-Phe-DTrp-Leu-(Nle);
p-HOPA-DTrp-Phe-DTrp-Leu-NH$_2$;
p-HOPA-DTrp-Phe-DTrp-Leu-Ψ(CH$_2$NH)Leu-NH$_2$;
DMePhe-DTrp-Phe-DTrp-Leu-Ψ(CH$_2$NH)Leu-NH$_2$;
DMePhe-DTrp-Tyr-DTrp-Leu-Ψ(CH$_2$NH)Leu-NH$_2$;
DTyr(Et)-DTrp-Phe-DTrp-Leu-Ψ(CH$_2$NH)Leu-NH$_2$;
DPhe-DTrp-Phe-DTrp-Leu-OH;
DMePhe-DTrp-Phe-DTrp-Leu-OH;

DPhe-DTrp-Phe-DTrp-Leu-MPA;
DMePhe-DTrp-Phe-DTrp-Leu-MPA;
DTyr-DTrp-Phe-DTrp-Leu-Ψ(CH$_2$NH)Leu-NH$_2$; and
DMePhe-DTrp-Phe-DTrp-Leu-Leu-NH$_2$.
where
HOPA=para-hydroxy-phenyl-acetic group
DMePhe=D-N-methyl-phenylalanine
MPA=2-amino-methylpentane.

In a preferred embodiment of Formula III, BKA is selected from

Lys-Lys-Arg-Pro-Hyp-Gly-Igl-Ser-DIgl-Oic;
DArg-Arg-Pro-Hyp-Gly-Igl-Ser-DIgl-Oic-Arg; or
DArg-Arg-Pro-Hyp-Gly-Thi-Ser-DTic-Oic-Arg; and
Y is DMePhe-DTrp-Phe-DTrp-Leu-Ψ(CH$_2$NH)Leu-NH$_2$.

Compounds of Formula III may be linked via any known method. For example, where both the BKA and the Y component are peptides, they may be linked via their N-terminals. Using the bis(imidoester) crosslinking agent dimethyl suberimidate, the following heterodimer may be synthesized:

DArg—Arg—Pro—Hyp—Gly—Igl—Ser—DIgl—Oic—Arg
|
SUIM
|
DPhe—DTrp—Phe—DTrp—Leu—OH.

Other examples of bis(imidoester) linking agents which may be used include dimethyl butyl-, -octyl-, -decyl-, -dodecyl-, and -tetradecylimidate, although any of the above described linker groups X may be used.

Further provided are dimerized neurokinin receptor antagonists of the formula $$Y_1—X—Y_2 \quad (IV)$$

where $Y_1$ and $Y_2$ are the same or different neurokinin receptor antagonists, as defined herein for Y. Several methods of linking these Y components are apparent from the disclosure and other methods will be known to those of skill in the art.

In addition, compounds of the formula $$(BKA)_n—X \quad (V)$$

where n is a whole number greater than 2, are also effective inhibitors of cancer cell growth. In a preferred embodiment, n is 3. Any of the X groups described herein may be modified for linking the trimers. Examples of linkages which may be used where n is 3, i.e., a trimer, include trissuccinimidoalkane and trissuccinimidoamide. Procedures for their preparation are described in Cheronis et al., *J. Med. Chem.* 35:1563–1572 (1992)).

Also described are methods of inhibiting lung cancer cell growth through administration of one or more of the compounds according to Formulas (I through V).

In a preferred method of inhibition, $BKA_1$, $BKA_2$ and BKA are peptides, preferably, selected from Arg-Pro-Pro-Gly-Phe-Ser-Pro-Phe-Arg (SEQ ID NO:1);
DArg-Arg-Pro-Hyp-Gly-Thi-Ser-DTic-Nig-Arg;
DArg-Arg-Pro-Hyp-Gly-Igl-Ser-DIgl-Oic-Arg;
Cys-DArg-Arg-Pro-Hyp-Gly-Igl-Ser-DIgl-Oic-Arg;
ε-Lys-DArg-Arg-Pro-Hyp-Gly-Igl-Ser-DIgl-Oic-Arg;
Gun-Gly-ε-Lys-Arg-Pro-Pro-Gly-Phe-Ser-Pro-Leu (SEQ ID NO:2);
Dhq-DArg-Arg-Pro-Hyp-Gly-ε-Lys-Ser-DCpg-CPg-Arg;
Dhq-ε-Lys-DArg-Arg-Pro-Hyp-Gly-Cpg-Ser-DCpg-CPg-Arg;
DArg-Arg-Pro-Hyp-Gly-Cpg-Ser-DCpg-CPg;
DArg-Cys-Pro-Hyp-Gly-Cpg-Ser-DCpg-Cpg;
DArg-Lys-Pro-Hyp-Gly-Cpg-Ser-DCpg-Cpg;
DArg-Arg-Pro-Hyp-Gly-Cpg-Ser-Tic-Cpg;
DArg-Arg-Pro-Hyp-Gly-Thi-Ser-Tic-Cpg;
DArg-Arg-Pro-Hyp-Gly-Cpg-Ser-DTic-Cpg;
DArg-Arg-Pro-Hyp-Gly-Thi-Ser-DTic-Cpg;
DArg-Arg-Pro-Hyp-Gly-Igl-Ser-DIgl-Oic;
    Arg-Pro-Hyp-Gly-Igl-Ser-DIgl-Leu;
DArg-Arg-Pro-Hyp-Gly-Igl-Ser-DIgl-Leu;
Gun- DArg-Arg-Pro-Hyp-Gly-Igl-Ser-DIgl-Oic;
DArg-Arg-Pro-Hyp-Gly-Thi-Ser-DIgl-Oic;
Gun- DArg-Arg-Pro-Hyp-Gly-Thi-Ser-DIgl-Oic;
DArg-Arg-Pro-Hyp-Gly-Igl-Ser-DTic-Cpg;
Lys-Arg-Pro-Hyp-Gly-Igl-Ser-DTic-Cpg;
Lys-Arg-Pro-Hyp-Gly-Igl-Ser-DIgl-Oic;
Lys- Lys-Arg-Pro-Hyp-Gly-Igl-Ser-DIgl-Oic;
DArg-Arg-Pro-Hyp-Gly-Phe-Cys-DPhe-Leu-Arg; and
DArg-Arg-Pro-Hyp-Gly-Thi-Ser-DTic-Oic-Arg.

In a particularly preferred embodiment, BKA is

DArg-Arg-Pro-Hyp-Gly-Igl-Ser-DIgl-Oic-Arg;
ε-Lys-DArg-Arg-Pro-Hyp-Gly-Igl-Ser-DIgl-Oic-Arg;
Lys-Lys-Arg-Pro-Hyp-Gly-Igl-Ser-DIgl-Oic; or
DArg-Arg-Pro-Hyp-Gly-Thi-Ser-DTic-Oic-Arg.

As described above, it is preferred that the dimers be comprised of modified bradykinin antagonist peptides that contain amino acids substituted on the α-carbon or on the α-nitrogen by 1-indanyl or 2-indanyl groups. These monomers are described in U.S. Pat. No. 5,648,336, incorporated herein by reference. In a preferred embodiment, the bradykinin antagonist peptide monomers contain indane-substituted amino acid residues at positions five, seven and eight of the bradykinin native sequence. According to this invention, the indane substituent can be on either the α-carbon (residues abbreviated Igl) or the nitrogen (residues abbreviated Nig) of the glycine residue, and the indane residue can be attached to the glycine moiety at either position 1 (Igla or Niga) or position 2 (Iglb or Nigb) of the indane group.

Nigb

As used herein, abbreviations of the natural amino acids are those accepted in the art (*Biochem. J.* 126:773 (1972)), and unless prefixed with D are all of the L-configuration (except glycine and MPIV, which are not optically active).

Abbreviations used for unnatural amino acids in Bradykinin analogs are indicated below:

| | |
|---|---|
| AC6 | 1-Aminocyclohexane-1-carboxylic acid |
| Alg | Allylglycine |
| Azt | Azetine-2-carboxylic acid (norproline) |
| CDF | p-Chloro-D-Phe |
| Chg | CyclohexylGly (α-Aminocyclohexaneacetic acid) |
| cLeu | 1-Aminocyclopentane-1-carboxylic acid (cycloleucine) |
| Cpg | CyclopentylGly (α-Aminocyclopentaneacetic acid) |
| Dhp | 3,4-Dehydro-Pro |
| DMF | 2,4-Dimethylphenylalanine |
| Eac | 6-Aminohexanoic acid (ε-aminocaproic acid) |
| FDF | p-Fluoro-DPhe |
| Gun | Guanidyl |
| HBQ | N5-(4-hydroxybutyl)-glutamine |
| Hig | Hexahydroindanylglycine |
| Hyp | trans-4-Hydroxy-Pro |
| Igla | α-(1-indanyl)glycine |
| Iglb | α-(2-indanyl)glycine |
| Inip | Isonipecotic acid (pipendine-4-carboxylic acid) |
| MDY | O-Methyl-DTyr |
| MPIV | 2,4-Methanoproline (2-Azabicyclo-(2,1,1)-hexane-1-carboxylic acid) |
| Nal | b-2-Napthyl-Ala |
| NChg | N-substituted cyclohexylglycine |
| Niga | N-(1-indanyl)glycine |
| Nigb | N-(2-indanyl)glycine |
| Nle | Norleucine |
| NMF | N-Methylphenylalanine |
| Oic | Octahydroindole-2-carboxylic acid |
| OMT | O-Methyl-Tyr |
| Pal | b-3-Pyridyl-Ala |
| PCF | p-Chloro-Phe |
| Pip | Pipecolic acid ("homo-Pro") |
| Pop | trans-4-PropoxyPro |
| Ser(SO$_4$) | Serine-O-sulfate |
| Suc | Succinyl |
| Thi | β-2-Thienyl-Ala |
| Thz | Thiazolidine-4-carboxylic acid |
| Tic | 1,2,3,4-Tetrahydroisoquinoline-3-carboxylic acid |

Abbreviations used for acylating groups, in addition to those described above, are as follows:

| | |
|---|---|
| Aaa- | 1-Adamantaneacetyl- |
| Ac- | Acetyl- |
| Aca- | 1-Adamantanecarbonyl- |
| Bz- | Benzoyl- |
| Cha- | Cyclohexaneacetyl- |
| Cpa- | Cyclopentaneacetyl- |
| Dca- | 2,2-Dicyclohexylacetyl- |
| Dhq- | 2,3-Dehydroquinuclidine-3-carbonyl- |
| Dpa- | 2,2-Diphenylacetyl- |
| Dpp- | 3,3-Diphenylpropionyl- |
| Nba- | Norbomane-2-acetyl- |
| Nbc- | 2-(cis-5-norbornene-endo-3-carbonyl)- |
| Nbi- | cis-5-norbornene-endo-2,3-dicarboximidyl- |
| Paa- | Phenylacetyl- |
| Pba- | 4-Phenylbutyryl- |
| Ppa- | 3-Phenylpropionyl- |
| Sin- | Sinapinyl- (3,5-dimethoxy-4-hydroxycinnamyl-) |

The description of peptide synthesis methods uses several abbreviations for standard solvents, reagents and procedures, defined as follows:

| | |
|---|---|
| BOP | Benzotriazolyloxy-tris-(dimethylamino)phosphonium hexafluorophosphate |
| BuOH | n-Butanol |
| DCC | Dicyclohexylcarbodiimide |
| DCM | Dichloromethane |
| DIC | Diisopropylcarbodiimide |
| DIEA | Diisopropylethyl amine |
| DMF | Dimethylformamide |
| HATU | O-(7-azabenzotriazol-1-yl)-1,1,3,3-tetramethyluronium hexafluorophosphate |
| HOAc | Acetic acid |
| MeOH | Methanol |
| OHMR | Hydroxymethylpolystyrene resin for peptide synthesis, 1% crosslinked. |
| TBTU | O-(benzotriazol-1-yl)-1,1,3,3-tetramethyluronium tetrafluoroborate |
| TEA | Triethyl amine |
| TFA | Trifluoroacetic acid |

The following abbreviations for blocking groups used in synthesis are:

| | |
|---|---|
| Boc | t-Butyloxycarbonyl |
| Tos | p-Toluenesulfonyl |
| Bzl | Benzyl ether |

The following abbreviations for standard techniques used are:

| | |
|---|---|
| AAA | Amino acid analysis (Stewart & Young p. 108) |
| CCD | Countercurrent distribution (Stewart & Young p. 96) |
| ELEC | Paper electrophoresis (Stewart & Young p. 117) |
| HPLC | High performance liquid chromatography (Stewart & Young, p. 100) |
| Kaiser test | Ninhydrin test for completeness of coupling reactions (Stewart & Young, p. 105) |
| SPPS | Solid phase peptide synthesis |
| TLC | Thin-layer chromatography (Stewart & Young, p. 103) |

The synthesis of peptides described herein, including preparation of appropriate amino acid derivatives, their activation and coupling to form peptides and methods for purification of peptides and determination of their purity are included in the general body of knowledge of peptide chemistry, as generally described in Houben-Weyl "Methoden der Organischen Chemie" Vol. 16, parts I & II, (1974) for solution-phase synthesis, and in "Solid Phase Peptide Synthesis" by Stewart and Young (1984) for synthesis by the solid phase method. A chemist skilled in the art of peptide synthesis would be able to synthesize the described peptides by standard solution methods or by manual or automatic solid phase methods.

In a majority of cases there appears to be a correlation between BK antagonist potency and the ability to inhibit cell growth. Therefore, it may be desirable to screen monomeric components for BK antagonism prior to dimerization as an indication of potential inhibitory action.

To determine bradykinin antagonist activity, the bradykinin antagonists may be assayed on isolated rat uterus in natural or induced estrus and on guinea pig ileum, according to the commonly accepted assay methods for bradykinin and related kinins as described by Trautschold (Handbook of Experimental Pharmacology, Vol. 25, Springer-Verlag, pp 53–55, (1969)) for inhibition of the myotropic activity of bradykinin. The inhibition potencies may be determined according to the commonly accepted manner, as described by Schild for antagonists of biologically active compounds (*Brit. J Pharmacol.* 2: 189 (1947)) and expressed as $pA_2$ values. In the assays, a dose-response curve is determined for the reference substance bradykinin. The dose of bradykinin which produces a half-maximal contraction of the tissue is the $ED_{50}$ dose. An amount of bradykinin equivalent to twice the $ED_{50}$ dose is administered to the tissue 30 seconds after the start of incubation of the tissue with a dose of antagonist. Doses of antagonist are increased in this protocol until the dose of antagonist is found which causes the tissue response to a double $ED_{50}$ dose of bradykinin in the presence of antagonist to equal the response of an $ED_{50}$ dose of bradykinin without antagonist. The $pA_2$ value represents the negative logarithm of the molar concentration of antagonist necessary to reduce the response to a double $ED_{50}$ dose of bradykinin to that of an $ED_{50}$ dose without antagonist. A change of one unit of $pA_2$ value represents an order of magnitude change in potency. For comparison, the negative logarithm of the dose of bradykinin that causes half-maximal contraction of the tissues, commonly known as the $pD_2$ value, is 7.9 on the rat uterus and 7.4 on the guinea pig ileum.

Binding assays using BK1, BK2 human receptor clones or BK2 guinea pig ileum smooth muscle membrane receptor preparations may also be used to screen potential components.

With regard to the heterodimeric compounds, i.e., those of the formula BKA—X—Y, and the dimeric NK1 and NK2 antagonists ($Y_1$—X—$Y_2$), the antagonistic properties of the neurokinin antagonist can be determined through assay methods well known in the art.

The effectiveness of the antagonist compounds in inhibiting cancer cell growth in vitro was determined using a panel of human lung cancer cell lines: SCLC—SHP77, H345 and NSCLC—A549, H450; breast carcinoma McF7, normal human epithelial BEAS and normal human skin fibroblast FS 15 were used to study the specificity and cytotoxicity of the BK antagonist dimers. Cell lines were treated with various concentrations of dimers for 5 to 7 days and cell viability were measured with routine MTT assay. Cells treated with BK dimers were also be evaluated for apoptosis using our newly developed cytometric technique.

The in vivo inhibitory effects of antagonists may be studied using tumor-bearing nude mice. A tumor model employing nude mice orthotopically implanted with human lung cancer cells wherein the antagonists are delivered by intratracheal instillation and aerosol inhalation may be used to evaluate the efficacy and feasibility of these antagonists as a means of treating human lung cancers. Control animals without tumor implantation may also be used to study the general side effects or cytotoxicity of the compounds. It is believed that aerosolized delivery or intratracheal instillation of the agents can produce effective dose accumulation in the area of lesion and reduce the overall systemic toxicity of the compounds in the animals than when the compound is delivered by intravenous injection.

Aerosolized BK antagonists have been used to treat animals with airway hyperreactivity. Thus, the study may allow evaluation of the possibility of using this kind of BK antagonist dimers for treating human pulmonary diseases such as asthma and other inflammatory diseases.

In addition to the above described embodiments, the following compounds are also disclosed herein (the monomer-linkers, dimers and trimers are linked via the available cysteine residue, unless otherwise indicated):

| | |
|---|---|
| CP-0088 | DArg—Arg—Pro—Hyp—Gly—Phe—Ser—DPhe—Leu—Arg |
| CP126 | [$Cys^6$]-CP-0088 or also<br>DArg—Arg—Pro—Hyp—Gly—Phe—Cys—DPhe—Leu—Arg |
| CP127 | N-hexyl succinimido - $(CP126)_2$ |
| CP162 | Bissuccinimidoethane - $(CP126)_2$ |
| CP166 | Bissuccinimidododecane - $(CP126)_2$ |
| CP172 | Bissuccinimidopropane - $(CP126)_2$ |
| CP174 | BSH - CP126 |
| CP211 | Bissuccinimidooctane - $(CP126)_2$ |
| CP229 | Bissuccinimidononane - $(CP126)_2$ |
| CP230 | Bissuccinimidodecane - $(CP126)_2$ |
| CP360 | BSH-(DArg—Arg—Pro—Hyp—Gly—Ala—Cys—DAla—Ala—Arg)$_2$ |
| CP394 | CP126 - (ESC) - $Lys^5$ (CT008) |
| CP397 | CP126 - (ESC) - $Lys^8$ (CT008) |
| CP411 | CP126 - (BSH) - $Cys^1$ (CT0022) |

| | |
|---|---|
| CP597 | DArg—Arg—Pro—Hyp—Gly—Thi—Ser—DTic—NChg—Arg |
| CT008 | DArg—DPro—Lys—Pro—Gln—Asn—DPhe—Phe—DTrp—Leu—Nle—CONH$_2$ |
| CT0022 | Asp—Tyr—DTrp—Val—DTrp—DTrp—Arg—CONH$_2$ |
| B9810 | Gun—Gly-ε-Lys—Arg—Pro—Pro—Gly—Phe—Ser—Pro—Leu (SEQ ID NO: 2) |
| B9878 | MOSI—DArg—Arg—Pro—Hyp—Gly—Cpg—Ser—DCpg—Cpg |
| CP352 | DArg—Arg—Pro—Hyp—Gly—Thi—Cys—DTic—Oic—Arg<br>⋮<br>BSH<br>⋮<br>DArg—Arg—Pro—Hyp—Gly—Thi—Cys—DTic—Oic |
| CP164 | Tris[2-γ-succinimidobutyramido)ethyl]amine—(CP126)$_3$ |
| CP171 | HO—CH$_2$—C—[(CH$_2$OC(O)CH$_2$CH$_2$—(CP126)]$_3$ |

The compounds may be administered topically, or by injection or infusion or as an oral suspension in an appropriate vehicle or as tablets, pills, capsules, caplets or the like, or preferably via intratracheal instillation or aerosol inhalation. The dosage and manner of administration will be defined by the application of the bradykinin antagonist and can be determined by routine methods of clinical testing to find the optimum dose. These doses are expected to be in the range of 0.001 mg/Kg to 100 mg/Kg of active compound.

The compounds are composed of amino acids which may form salts due to their acidic or basic nature, and any pharmacologically acceptable salt derived from the compounds described in this invention such as hydrochlorides, acetates, phosphates, maleates, citrates, benzoates, salicylates, succinates, ascorbates and the like, including HCl, trifluoroacetic acid (TFA), and HOAc, are considered an extension of this invention. A common tactic in medicinal chemistry is to modify known drug substances which are peptide based to form esters or amides which exhibit greater bioavailability. Prodrugs derived from the compounds disclosed here are therefore considered an obvious extension of this invention. Methods for designing and preparing prodrugs are described in detail in the medicinal chemical literature.

EXAMPLES

Example I

Synthesis of Dimers of Bradykinin Antagonists

Dimers were synthesized on either solid phase resin support or in solution.

Succinyl-bis-peptide Dimers on Resin (B9132 and B9572 (B168)

A ten-fold excess of succinic anhydride with a ten-fold excess of triethylamine was allowed to react with the peptide-resin to give the succinyl peptide (mono-adduct) on the peptide-resin. Then the pure, neutralized peptide monomer was allowed to react in DMF with the BOP-, TBTU-, or HATU-activated succinyl-peptide on the resin to give the succinyl-bis peptide dimer still attached to the resin. The finished peptide-dimers were cleaved form the resin using standard HF procedures (Stewart et al., "Laboratory Techniques in Solid-Phase Peptide Synthesis" in Solid-Phase Peptide Synthesis, 2nd ed., Pierce Chemical Co., Rockford, Ill., pp. 71–72 (1984)). The free peptides were extracted with acetic acid, lyophilized and purified with reverse-phase HPLC.

Suberyl-bis-peptide Dimers on Resin (B9860 HPLC#3 and HPLC#4)

A five-fold excess of dissuccinimidyl suberate (DDS) with a 1–2 fold excess on N,N-diisopropyl-ethylamine (DIEA) in DMF was allowed to react with the peptide resin having a free ε-Lys group (B9810) was allowed to react with the suberyl-peptide on the resin to give the Sub-bis-peptide dimer still attached to the resin. The finished peptides were cleaved from the resin using standard HF procedures (Stewart). Free peptides were extracted with acetic acid, lyophilized and purified by preparative reversed-phase HPLC. The HPLC separation gave hetero-(B9860HPLC#3) and homo-dimer (B9860 HPLC#4).

Suberyl-bis-peptide Dimers in Solution (B9832)

One equivalent of neutralized peptide with 10 equivalents of DIEA and 0.75–1 equivalents of disuccinimidyl suberate (DSS) were allowed to react overnight in DMF at room temperature, and the resulting dimer was purified by preparative reversed-phase HPLC.

Bis-succinimidohexane Peptide Dimers in Solution (B9834 and B9836)

One equivalent of Cys-containing peptide monomer salt, ten equivalents of DIEA and 0.75 equivalents of bismaleimidohexane (BMH) linker were allowed to react overnight in DMF. The resulting vissuccinimidoalkane peptide diemrs were purified by preparative reversed-phase HPLC.

Using the same chemistry, dimers were synthesized with longer linkers:

BSO=bissuccinimidooctane
BSN=bissuccinimidononane
BSD=bissuccinimidodecane.

Suberimidyl-bis-peptide Dimers in Solution (B9830, B9870, B9872, B9878)

One equivalent of peptide monomer salt, 15 equivalents of DIEA and 1 equivalent of dimethyl suberimidate0.2HCl (DMS) were stirred overnight in DMF at room temperature. The DMF was removed in vacuo and the residue was purified by reversed-phase HPLC. The HPLC separation gave the MOSI-monomers and the SUIM-bis-diemrs generally in a 1:2 ratio.

Using the same chemistry, dimers were synthesized with longerlinkers using the following linking agents:

Dimethyl sebacimidate (10-carbon linker)

Dimethyl decanedicarboximidate (12-carbon linker)

Dimethyl dodecanedicarboximidate (14-carbon linker).

Example II

Cys-(Succinimido-N-Caproyl)-Lys-BK2/NK1 Antagonist Heterodimers

To a preparation of L-Lys(Fmoc)-containing $NK_1$ peptide antagonist-resin (MBHA, 0.5 mmole peptide) was added 50% piperidine in DMF (ca. 20 mL). The resulting mixture was bubbled gently with $N_2$ (g) for 20 minutes to afford complete removal of the Lys(Fmoc) protecing group and then the peptide-resing was washed well with DMF. The peptide-resin was resuspended in DMF and 1.5 equivalents of EMCS (epsilon-maleimido-n-caproic acid N-hydroxysuccinimide ester) were added. The acylation reaction was allowed to proceed at room temperature for 2–3 hours (verification of compoete acylation accomplished with the Kaiser test) after which time the peptide-resin was washed well with DMF, then with 10% (v/v) $NH_4HCO_3$/DMF ($NH_4HCO_3$ stock concentration: 0.1M, pH 8). The $BK_2$ antagonist CP126, 3 equivalents in 10% (v/v) $NH_4HCO_3$/DMF was added to the maleimido-containing peptide-resin and the subsequent conjugate addition (1,4-addition or Michael reaction) allowed to proceed at room termperature for several hours. The pepitde-resin was then washed well (successively) with 10% (v/v) $NH_4HCO_3$/DMF, DMF and dichloromethane. Following extensive drying in vacuo, the Cys-(succinimido-n-caproyl)-Lys $BK_2$/$NK_1$ antagonist heterodimer was deprotected/cleaved from the peptide-resin with anhydrous HF at 0° C. and then purified by preparative reversed -phase HPLC. Lyophilization afforded the pure peptide in 50–60% yield as a fluffy, white powder.

Example III

Cys-[Bis(Succinimido)Hexane])-Cys-BK2/NK2 Antagonist Heterodimers

To a mixture of Cys-containing $NK_2$ peptide antagonist (1 equivalent) and bis(malameimido)hexane (BMH, 2 equivalents) in DMF (ca. 21 mL per mmole of peptide) was added 10 volumes of $NH_4HCO_3$ (pH 8). The reaction mixture was stirred at room temperature for seveal hours (monitored periodically by analytical reversed-phase HPLC) and the resulting S-[(N-hexyllmaleimido)succinimido] derivative of the $NK_2$ antagonist purified by preparative reversed-phase HPLC. The resulting peptide, isolated in approximately 70% yield after lyophilization, was then combined with the $BK_2$ antaognist CP126 (1.5 equivalents) in DMF (same mL/mmole as specified above). Ten volumes of $NH_4HCO_3$ (pH 8) were added and the dimerization allolwed to procedd for several hours at room termperature. The resulting Cys-[bis(Succinimido)Hexane])-Cys BK2/NK2 antagonist hterodimer was purified by preparative reversed-phase HPLC and lyophilized to yield a white, fluffy powder. OVerall yields ranged from 40–50%.

Example IV

BK1/BK2 Binding Assays

Human lung fibroblasts IMR-90 cells were obtained from ATCC and propagated in DMEM media in 850 mm roller bottles until confluent. Three hours prior to harvesting, the cells were treated with Interleukin lb (200 pg/ml). Human BK2 clones were propagated in F12 media until confluent. Preparation of membranes for binding assays was carried out by scraping cells from roller bottles in ice cold PBS and centrifuging at 1000 xg, at 4° C. for 15 minutes. The supernatant was discarded and pellet resuspended in Buffer A consisting of 25 mM TES(PH 6.8) with 2 µM 1,10-Phenanthroline, and centrifuged at 27,000 xg for 15 min. this was then repeated. The final pellet was resuspended in Buffer B (Buffer A with 2 µM Captopril, 140 µg/Ml Bacitracin, 0.1%BSA), and stored in 1 ml aliquots, frozen at −20° C. until needed.

Binding assays were performed by incubating human clone membranes with 0.3 nM $^3$H-Bradykinin or IMR-90 membranes with 0.5 nM $^3$H-des-Arg$^9$-Kallidin in the presence of the peptides in assay buffer (Buffer B with 1 mM Dithiotreitol), at room temperature, for 45 minutes. All test compound dilutions were in triplicate. Assays were harvested by quick filtration in a Tomtec Harvester 96, with ice cold wash buffer consisting of 10 mM Tris/HCl, pH 7.5, 100 MM NaCl, 0.02%BSA, onto Wallec printed glassfiber Filtermat "B", which had been pre-soaked with 0.1% PEI and previously air-dried. Filtermats were counted in 9.5 mls Wallec Beta-Plate Scint, in Wallec 1450 MicroBeta Counter.

Results are shown in Table I

TABLE I

Receptor binding data - Human B1/B2; GPI B2

| Compound | Binding: Human B1 Receptor - $pIC_{50}$ | Binding: Human B2 Receptor - $pIC_{50}$ | Binding:GPI (B2) $pIC_{50}$ |
| --- | --- | --- | --- |
| B9572 |  | 8.7 | 8.5 |
| B9830 | 6 | 8.3 | 8.6 |
| B9832 | 6 | 8.4 | 8.9 |
| B9834 | 7.2 | 8.4 | 7.9 |
| B9836 | 7.9 | 9.1 | 8.8 |
| B9860 (HPLC3) | 8.5 | 9.3 | 9 |
| B9860 (HPLC4) | 8.0 | 8.8 | 8.5 |
| B9870 (HPLC1) | 7.8 | 9.1 | 9.1 |
| B9870 (HPLC2) | 7.9 | 8.4 | 8.3 |
| B9872 (HPLC2) | NT | 9.5 | 9.7 |
| B9872 (HPLC3) | NT | 8.8 | 9.0 |
| B9878 (HPLC2) | 8.5 | 6.4 | 6.1 |
| B9878 (HPLC3) | 8.9 | 6.5 | 6.5 |

$pIC_{50}$ = -log of the $IC_{50}$ (concentration in molar which inhibits tritiated ligand binding by 50%)

Example V

Rat Uterus Assay for B2 Receptor for B2/NK1 and B2/NK2 Compounds

Female rats were pretreated with stilboestrol, 100 µg/kg s.c. Eighteen hours later the animals were sacrificed by $CO_2$ asphyxiation. The uterine horns were removed and attached to tissue holder swhich were placed in 5 ml tissue baths containing DeJalon's solution at 31° C. and bubbled with air. Tissues were placed under 1 gm isometric resting tension. Cumulative concentration effet curves were constructed to bradykinin in the absence and presence of increasing concentrations of the antagonist at 1 h intervals. $pA_2$ values were calculated according to the method of Schild .

Example VI

NK1 Assay for BK/NK1 Compounds—Guinea Pig Ileum

Male guinea-pigs were sacrificed by $CO_2$ asphyxiation. The ileum was remoed and cleaned of fat and mesenteric tissue. Longitudinal sections, 25 mm in length wer attached to tissue holders and placed in 5 ml tissue baths containing Kreb's solution at 37° C. and bubbled with 95%$O_2$/5%$CO_2$. Tissues were placed under 2 gm isometric resting tension. Following a 1 h incubation period, cumulative concentration effect curves were constructed to substance P in the absence and presence of increasing concentrations of the antagonist at 1 h intervals. Compound CP394 yielded a $pA_2$ value of 5.8.

Example VII
NK2 Assay for BK/NK2 Compounds—Rabbit Pulmonary Artery

Female New Zealand White Rabbits were sacrificed by $CO_2$ asphyxiation. The pulmonary artery was removed and prepared as vascular rings. The preparations were secured on tissue holders and placed under 1 gm isometric resting tension in 5 ml tissue bathes containing Krebs solution at 37° C. and bubbled with $95\%O_2/5\%CO_2$. Cumulative concentration effect curves were constructed to neurokinin A in the absence and presence of increasing concentrations of the antagonists. Compound CP411 yielded a $pA_2$ value of 5.5.

Example VIII
Calcium Flux Assays

Cells were loaded with the calcium marker Indo-1 AM (Molecular Probes, Eugene, Oreg.) according to the methods described previously (Bunn et al: Proc. Natl. Acad. Sci. USA. Vol, 87, 2162–2166, 1990). Briefly, mechanically dispersed single cell suspensions of plateau phase cells (7 days after splitting) were suspended in 20 mM HEPES/BSS buffer (20 mM Hepes/140 mM NaCl/5mM KCI/1 mM $MgCl_2/5$ mM Glucose) adjusted to pH 6,8 at 37° C. The acetoxymethyl ester form of Indo-1 (Indo-AM) at 5 $\mu$M was incubated with the cells for 30 min at 37° C. and then diluted with 1:1 with 20 mM HEPES/BSS buffer, pH 7.4 to raise the final pH to 7.1 followed by a second 30-min incubation at 37° C. The cells were then washed twice in HEPES/BSS buffer, pH7.4 (37° C.) containing dextrose and were resuspened to $1 \times 10^6$ cells per ml prior to flow cytometric analysis, which was performed with an EPICS 752 cell sorter (Coulter).

UV excitation (80 mW at 360 nm) was delivered by a model INNOVA 90/5 argon ion laser (Coherent, Palo Alto, Calif.). Violet emission fluorescence intensity (397–417 nm), which is emitted from calcium-bound indo-1, was obtained with a 410 band pass filter (Oriel, Stratford, Conn.) and blue emission fluorescence (480–500 nm), which is emitted from free indo-1, was obtained with a 490 band pass filter (Oriel). Thus, the ratio of the 410 nm fluorescence/490 nm fluorescence constitutes a measure of the changes in calcium ions liberated form intracellular stores (Endoplasmic reticulum) in response to various stimuli. Viable, loaded cells were distinguished by the machine form debris, dead cells, and unloaded cells by forward angle and 90° light scatter and 490 nm fluorescence. The ratio of 410 nm fluorescence /490 nm fluorescence emission was calculated digitally for each cell by the MDADS hardware and displayed on a linear scale. Data were collected by the MDADS computer including 410 nm and 490 nm fluorescence intensities and the ratio of 410/490 fluorescence intensity was secured as a function of time. For each experiment, measurements were first performed on unstimulated cells to establish the base line followed by the addition of each specific bradykinin antagonist first and then 3–5 min later followed by the bradykinin agonist. Cell flow was halted briefly (approximately 10 sec) for the administration of each peptide. The data were analyzed by a program developed by Philip Jewett.

Example IX
Colorimetric MTT (tetrazolium) Assay

Cellular growth and survival was measured by a rapid colorimetric assay, based on the tetrazolium salt MTT, (3-(4,5-dimethylthiazol-2-yl)-2,5-diphenyl tetrazolium bromide), developed by Mosmann (J. of Immun. Methods, 65, 55–63, 1983) with minor modifications. Briefly, 1,000 normal lung fibroblasts or normal epithelial BEAS-2B cells, 1,000 or 5,000 viable NSCLC cell and 10,000 viable SCLC cell were plated in a 100 $\mu$l volume of growth medium in 96 well flat-bottomed microtiter plates. The cells were allowed to recover overnight. Bradykinin antagonists at various concentrations were added to the cells in triplicates and the plates were incubated at 37° C., 5% $CO_2$ with 100% humidity. Control cells were treated in a same way without the antagonists. All wells had a final volume of 200 $\mu$l and the plates were incubated for 3–4 days allowing sufficient time for the cell replicaiton and antagonist induced cell death to occur. On the 5th day, 25 $\mu$l of a 2 mg/ml solution of the tetrazolium salt MTT (Sigma Chemical CO, St. Louis, Mo.) dissolved in RPM1640 was added to each well. The microtiter plate was incubated for 4 h at 37° C. The supernate was removed and the dark blue formazan complex was solubilized by adding 100 $\mu$l of 0.02 N HCl in 75% isopropanol to all wells. Absorbance at 490 nm was immediately determined using a scannning multiwell plate reader.

Example X

Data

Figure 1:
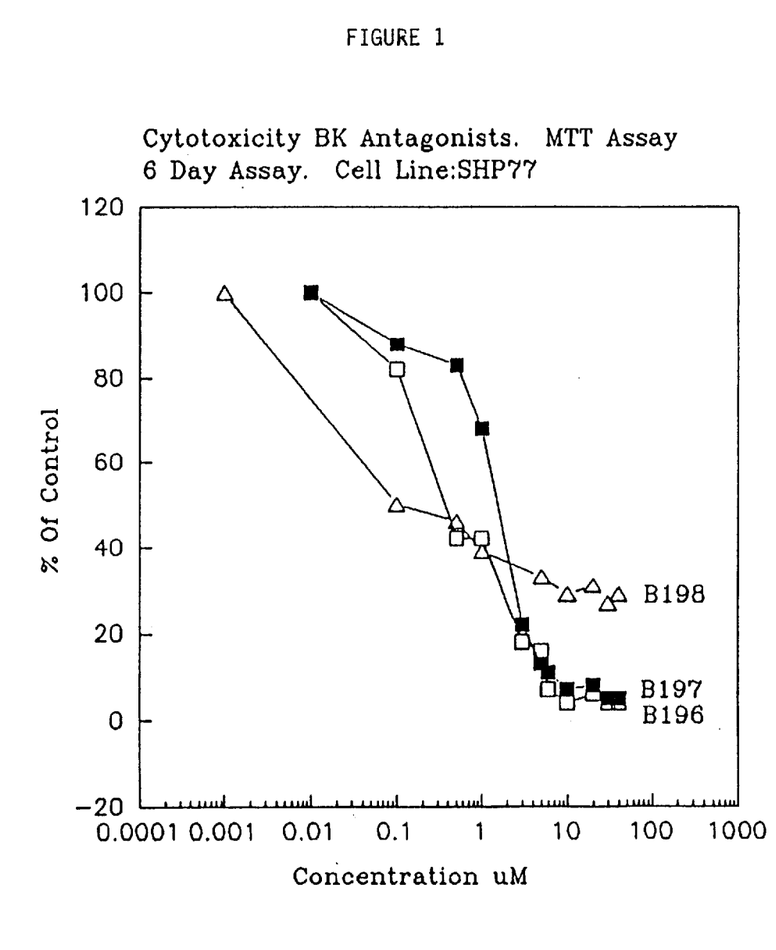
FIG. 1 shows the effect of compounds B196, B197 and B198 on SCLC growth.
Figure 2:
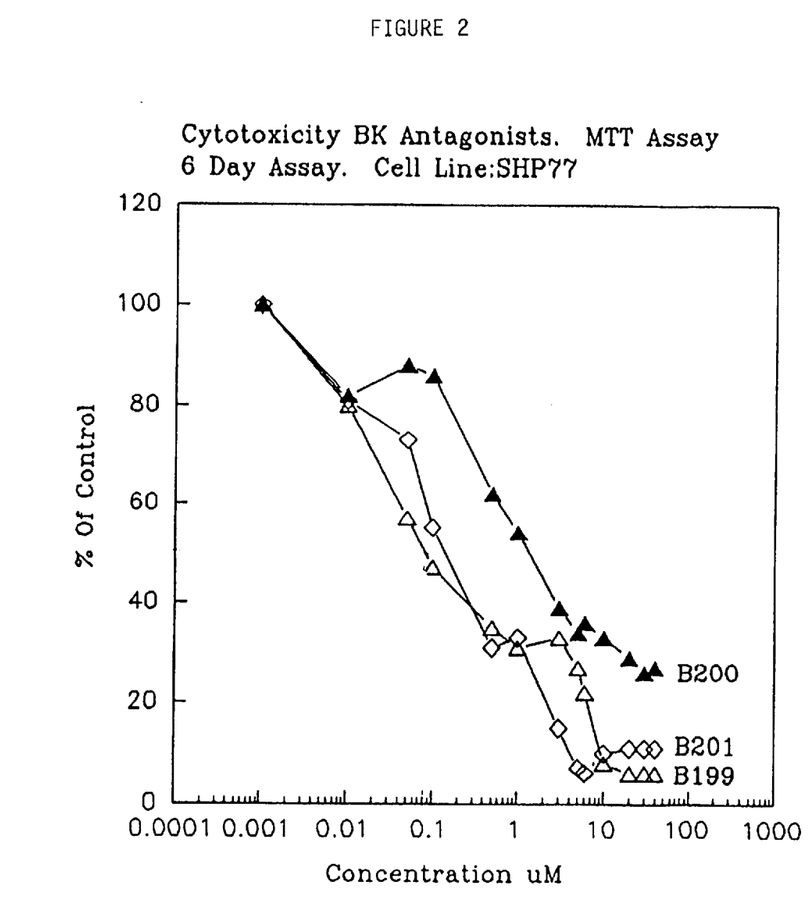
FIG. 2 shows the effect of compounds B199, B200 and B201 on SCLC growth.

Table II below shows the effects of several second and third generation bradykinin antagonists on the cell growth of the SCLC cell line SHP-77 in an MTT assay. The second generation dimer CP-0127 and the second generation monomer B1 16 (HOE 140) had little effect on SCLC growth in concentration up to 40 $\mu$M. Likewise, a newly synthesized monomer termed B203 had little effect on SCLC growth in concentration up to 40 $\mu$M. In contrast, the homodimer of B203, termed B204, linked with a suberimido group through the DArg$^0$ amino acids produced 100% growth inhibition at 40 $\mu$M. Several other third generation dimers were studied (e.g., B168, B199, B201 and corresponding monomers, e.g., B202) and found to be highly effective in inhibiting the growth of SCLC cell lines. The most potent of these compounds (B199, B201) had $IC_{50}$ concentrations $\leq 100$ nM. (See FIGS. 1 and 2). The cytotoxicity was specific as these compounds produced no effect on the growth of fibroblasts and breast cancer cell lines at concentrations up to 10 $\mu$M. (Data not shown).

To understand the mechanism of the growth inhibition of these compounds, the effects on BK and cholecystokinin (CCK) induced signal transduction, SCLC growth and plasma stability were compared. The table below shows that the potency of the second (B 116, CP-0127) and third generation (B 194–B201) antagonists were similar for inhibition of BK induced calcium signaling (0.01 to 0.15 $\mu$M) and all nine tested did not inhibit signaling induced by CCK or gastrin. Many of the third generation compounds (B197–B204) were stable in plasma (>24h), as was the second generation B116. Thus, plasma stability could not account for the increased growth inhibitory effects of many of the third generation dimers which had $IC_{50}$'s of about 100 nM for SCLC growth in MTT assays.

TABLE II

Effect of Bradykinin Antagonists on Calcium Flux in Response to BK and CCK, on Growth of SCLC Cell Lines in MTT Assay and on Stability in Plasma

| Compound | $IC_{50}$ ($\mu M$) $Ca^{2+}$ (BK) | $IC_{50}$ ($\mu M$) MTT | Plasma $t_{1/2}$ (hr) | % Inhibition CCK $Ca^{2+}$ |
|---|---|---|---|---|
| B116 | 0.01 | >40 | >24 | 0 |
| CP-0127 | 0.5 | >40 | <1 | 0 |
| B168 | .04 | 15 | NT | NT |
| B194 9830HPLC 9452DMS9452 | 0.2 | 0.1 | 1 | 0 |
| B195 9832HPLC 9452DSS9452 | 0.09 | 0.15 | 6 | NT |
| B196 9834HPLC 9722BMH9722 | 0.07 | 0.4 | 1 | 8 |
| B197 9836HPLC 9754BMH9754 | 0.05 | 0.2 | >24 | 2 |
| B198 9860HPLC3 | 0.15 | 0.10 | >24 | 0 |
| B199 9860HPLC4 | 0.08 | 0.08 | >24 | 0 |
| B200 9870HPLC1 | 0.02 | 1.0 | >24 | 0 |
| B201 9870HPLC2 | 0.02 | 0.15 | >24 | 0 |
| B202 9792(47–57) | 0.1 | >10 | NT | NT |
| B203 9872HPLC2 | 0.03 | >40 | NT | NT |
| B204 9872HPLC3 | 0.008 | 35 | NT | NT |

NT = not tested

Without being bound by any particular theory regarding mechanism of action, these data indicate that these dimerized BK antagonists inhibit growth by a mechanism other than interruption of the calcium response such as induction of apoptosis. Therefore, various SCLC cell lines were incubated with inhibitory concentrations of the dimerized BK antagonists and examined for their apoptotic effects. Dimeric compounds such as B197 induced an apoptotic response in SCLC cell lines whereas monomeric compounds such as HOE 140 (B 116) produced no growth inhibition or apoptotic response. It has not yet been determined the mechanism of the apoptotic response (data not shown). However, it is suspected that the antagonists are binding to a non-peptide binding site on the peptide receptor and produce discordant signaling with activation of the matk/erk-kinase (MEKK) pathway.

All cited patents, patent documents and publications are incorporated by reference herein as though fully set forth.

We claim:

1. A bradykinin antagonist compound of the general formula:

BKA₁—X—BKA₂, wherein BKA₁ and BKA₂ are independently selected from the following:
Arg-Pro-Pro-Gly-Phe-Ser-Pro-Phe-Arg (SEQ ID NO:1);
DArg-Arg-Pro-Hyp-Gly-Thi-Ser-DTic-Nig-Arg;
DArg-Arg-Pro-Hyp-Gly-Igl-Ser-DIgl-Oic-Arg;
Cys-DArg-Arg-Pro-Hyp-Gly-Igl-Ser-DIgl-Oic-Arg;
ε-Lys-DArg-Arg-Pro-Hyp-Gly-Igl-Ser-DIgl-Oic-Arg;
Gun-Gly-8-Lys-Arg-Pro-Pro-Gly-Phe-Ser-Pro-Leu (SEQ ID NO:2);
Dhq-DArg-Arg-Pro-Hyp-Gly-ε-Lys-Ser-DCpg-CPg-Arg;
Dhq-ε-Lys-DArg-Arg-Pro-Hyp-Gly-Cpg-Ser-DCpg-CPg-Arg;
DArg-Arg-Pro-Hyp-Gly-Cpg-Ser-DCpg-CPg;
DArg-Cys-Pro-Hyp-Gly-Cpg-Ser-DCpg-Cpg;
DArg-Lys-Pro-Hyp-Gly-Cpg-Ser-DCpg-Cpg;
DArg-Arg-Pro-Hyp-Gly-Cpg-Ser-Tic-Cpg;
DArg-Arg-Pro-Hyp-Gly-Thi-Ser-Tic-Cpg;
DArg-Arg-Pro-Hyp-Gly-Cpg-Ser-DTic-Cpg;
DArg-Arg-Pro-Hyp-Gly-Thi-Ser-DTic-Cpg;
DArg-Arg-Pro-Hyp-Gly-Igl-Ser-DIgl-Oic;
Arg-Pro-Hyp-Gly-Igl-Ser-DIgl-Leu;
DArg-Arg-Pro-Hyp-Gly-Igl-Ser-DIgl-Leu;
Gun- DArg-Arg-Pro-Hyp-Gly-Igl-Ser-DIgl-Oic;
DArg-Arg-Pro-Hyp-Gly-Thi-Ser-DIgl-Oic;
Gun- DArg-Arg-Pro-Hyp-Gly-Thi-Ser-DIgl-Oic;
DArg-Arg-Pro-Hyp-Gly-Igl-Ser-DTic-Cpg;
Lys-Arg-Pro-Hyp-Gly-Igl-Ser-DTic-Cpg;
Lys-Arg-Pro-Hyp-Gly-Igl-Ser-DIgl-Oic;
Lys- Lys-Arg-Pro-Hyp-Gly-Igl-Ser-DIgl-Oic; and
DArg-Arg-Pro-Hyp-Gly-Thi-Ser-DTic-Oic;

and

X is a linker group.

2. The bradykinin antagonist according to claim 1 wherein X is a bissuccinimidoalkyl,bissuccinimidoalkenyl, bissuccinimidoamino,aminocaproicacid-succinyl, suberyl, bis(imidyl)alkyl, bis(imidyl)alkenyl, epsilon succinimido N-caproyl, or methoxy-suberimido linker.

3. The bradykinin antagonist according to claim 2 wherein X is BSH, BSD, SUIM or MOSI.

4. The bradykinin antagonist according to claim 2 wherein X comprises an alkyl group of 12 to 18 carbons.

5. The bradykinin antagonist according to claim 1 wherein BKA₁ and BKA₂ are N-terminally linked.

6. The bradykinin antagonist according to claim 1 wherein serine is replaced with cysteine or lysine and internally linked therethrough.

7. The bradykinin antagonist according to claim 1 selected from:

-continued

Dhq—DArg—Arg—Pro—Hyp—Gly—Lys—Ser—DCpg—CPg—Arg
                                    |
                                    Suc
                                    |
Dhq—DArg—Arg—Pro—Hyp—Gly—Lys—Ser—DCpg—CPg—Arg; and Suim—(DArg—Arg—Pro—Hyp—Gly—Cpg—Ser—DCpg—CPg)$_2$.

8. The bradykinin antagonist according to claim 1 wherein BKA$_1$ and BKA$_2$ are selected from
DArg-Arg-Pro-Hyp-Gly-Igl-Ser-DIgl-Oic-Arg, and
Lys-DArg-Arg-Pro-Hyp-Gly-Igl-Ser-DIgl-Oic-Arg.

9. The bradykinin antagonist according to claim 8 wherein BKA$_1$—X—BKA$_2$ is

Lys—DArg—Arg—Pro—Hyp—Gly—Igl—Ser—DIgl—Oic—Arg
 |
 SUB
 |
Lys—DArg—Arg—Pro—Hyp—Gly—Igl—Ser—DIgl—Oic—Arg; or

DArg—Arg—Pro—Hyp—Gly—Igl—Ser—DIgl—Oic—Arg
 |
 SUIM
 |
DArg—Arg—Pro—Hyp—Gly—Igl—Ser—DIgl—Oic—Arg.

10. A therapeutic method of inhibiting lung cancer cell growth comprising administering to a host in need of such treatment a therapeutically effective amount of one or more of the following compounds.

BKA$_1$—X—BKA$_2$   I;

wherein BKA$_1$ and BKA$_2$ are the same or different bradykinin antagonists, and X is a linker.

11. The method according to claim 10 wherein BKA$_1$ and BKA$_2$ are peptides.

12. The method according to claim 11 wherein BKA$_1$ and BKA$_2$ are selected from
Arg-Pro-Pro-Gly-Phe-Ser-Pro-Phe-Arg (SEQ ID NO:1);
DArg-Arg-Pro-Hyp-Gly-Thi-Ser-DTic-Nig-Arg;
DArg-Arg-Pro-Hyp-Gly-Igl-Ser-DIgl-Oic-Arg;
Cys-DArg-Arg-Pro-Hyp-Gly-Igl-Ser-DIgl-Oic-Arg;
ε-Lys-DArg-Arg-Pro-Hyp-Gly-Igl-Ser-DIgl-Oic-Arg;
Gun-Gly-ε-Lys-Arg-Pro-Pro-Gly-Phe-Ser-Pro-Leu (SEQ ID NO:2);
Dhq-DArg-Arg-Pro-Hyp-Gly-ε-Lys-Ser-DCpg-CPg-Arg;
Dhq-ε-Lys-DArg-Arg-Pro-Hyp-Gly-Cpg-Ser-DCpg-CPg-Arg;
DArg-Arg-Pro-Hyp-Gly-Cpg-Ser-DCpg-CPg;
DArg-Cys-Pro-Hyp-Gly-Cpg- Ser-DCpg-Cpg;
DArg-Lys-Pro-Hyp-Gly-Cpg-Ser-DCpg-Cpg;
DArg-Arg-Pro-Hyp-Gly-Cpg-Ser-Tic-Cpg;
DArg-Arg-Pro-Hyp-Gly-Thi-Ser-Tic-Cpg;
DArg-Arg-Pro-Hyp-Gly-Cpg-Ser-DTic-Cpg;
DArg-Arg-Pro-Hyp-Gly-Thi-Ser-DTic-Cpg;
DArg-Arg-Pro-Hyp-Gly-Igl-Ser-DIgl-Oic;
Arg-Pro-Hyp-Gly-Igl-Ser-DIgl-Leu;
DArg-Arg-Pro-Hyp-Gly-Igl-Ser-DIgl-Leu;
Gun- DArg-Arg-Pro-Hyp-Gly-Igl-Ser-DIgl-Oic;
DArg-Arg-Pro-Hyp-Gly-Thi-Ser-DIgl-Oic;
Gun- DArg-Arg-Pro-Hyp-Gly-Thi-Ser-DIgl-Oic;
DArg-Arg-Pro-Hyp-Gly-Igl-Ser-DTic-Cpg;
Lys-Arg-Pro-Hyp-Gly-Igl-Ser-DTic-Cpg;
Lys-Arg-Pro-Hyp-Gly-Igl-Ser-DIgl-Oic;
Lys- Lys-Arg-Pro-Hyp-Gly-Igl-Ser-DIgl-Oic;
DArg-Arg-Pro-Hyp-Gly-Phe-Cys-DPhe-Leu-Arg; and
DArg-Arg-Pro-Hyp-Gly-Thi-Ser-DTic-Oic-Arg.

13. The method according to claim 12 wherein BKA$_1$ and BKA$_2$ are selected from
DArg-Arg-Pro-Hyp-Gly-Igl-Ser-DIgl-Oic-Arg;
ε-Lys-DArg-Arg-Pro-Hyp-Gly-Igl-Ser-DIgl-Oic-Arg;
Lys-Lys-Arg-Pro-Hyp-Gly-Igl-Ser-DIgl-Oic; and
DArg-Arg-Pro-Hyp-Gly-Thi-Ser-DTic-Oic-Arg.

14. The method according to claim 13 wherein BKA$_1$—X—BKA$_2$ is

Lys—DArg—Arg—Pro—Hyp—Gly—Igl—Ser—DIgl—Oic—Arg
 |
 SUB
 |
Lys—DArg—Arg—Pro—Hyp—Gly—Igl—Ser—DIgl—Oic—Arg;

DArg—Arg—Pro—Hyp—Gly—Igl—Ser—DIgl—Oic—Arg
 |
 SUIM
 |
DArg—Arg—Pro—Hyp—Gly—Igl—Ser—DIgl—Oic—Arg;

MOSI—(DArg—Arg—Pro—Hyp—Gly—Thi—Ser—DTic—Oic)$_2$; or

MOSI—(Lys—Lys—Arg—Pro—Hyp—Gly—Igl—Ser—DIgl—Oic)$_2$.

15. The method according to claim 10 wherein BKA$_1$ and BKA$_2$ are N-terminally linked.

16. The method according to claim 12 wherein serine, if present, is replaced with cysteine or lysine and internally linked therethrough.

17. The method according to claim 10 wherein X is a bissuccinimidoalkyl; bissuccunimidoalkenyl, bissuccinimidoamino, aminocaproic acid-succinyl, suberyl, bis(imidyl)alkyl, bis(imidyl)alkenyl, epsilon succinimido N-caproyl, or methoxy-suberimido linker.

18. The method according to claim 10 wherein the cancer cells are small cell lung carcininoma.

19. The method according to claim 10 wherein the bradykinin antagonist is administered via intratracheal instillation.

20. The method according to claim 10 wherein the bradykinin antagonist is administered via aerosol inhalation.

* * * * *

SEQUENCE LISTING ( 1 ) GENERAL INFORMATION:

( i i i ) NUMBER OF SEQUENCES: 2

( 2 ) INFORMATION FOR SEQ ID NO: 1:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO: 1:

Arg Pro Pro Gly Phe Ser Pro Phe Arg
1               5

( 2 ) INFORMATION FOR SEQ ID NO: 2:

( i ) SEQUENCE CHARACTERISTICS:
        ( A ) LENGTH: 11 amino acids
        ( B ) TYPE: amino acid
        ( C ) STRANDEDNESS: single
        ( D ) TOPOLOGY: linear     ( i i ) MOLECULE TYPE: peptide     ( x i ) SEQUENCE DESCRIPTION: SEQ ID NO: 2:

Xaa Gly Lys Arg Pro Pro Gly Phe Ser Pro Leu
1               5                   10